United States Patent [19]

Mazanec et al.

[11] Patent Number: 4,616,000

[45] Date of Patent: Oct. 7, 1986

[54] COPPER BERYLLIUM-CONTAINING CATALYSTS FOR THE PRODUCTION OF ALCOHOLS

[75] Inventors: Terry J. Mazanec; John G. Frye, Jr., both of Solon; Harley F. Hardman, Lyndhurst, all of Ohio

[73] Assignee: The Standard Oil Company, Cleveland, Ohio

[21] Appl. No.: 763,868

[22] Filed: Aug. 9, 1985

[51] Int. Cl.[4] .......................... B01J 23/02; B01J 23/72
[52] U.S. Cl. .................................... 502/341; 502/244; 502/302; 502/303; 502/304; 502/306; 502/324; 502/328; 502/340; 502/343; 502/345; 518/713
[58] Field of Search ............... 502/244, 302, 303, 304, 502/306, 340, 341, 345, 324, 328, 343; 518/713

[56] References Cited

U.S. PATENT DOCUMENTS 2,767,202 10/1956 Rottig .................................. 518/713
3,197,418 7/1965 Maebashi et al. ................ 502/345 X
4,408,071 10/1983 Pedersen et al. ................. 502/212 X

*Primary Examiner*—W. J. Shine
*Attorney, Agent, or Firm*—Salvatore P. Pace; David J. Untener; Larry W. Evans

[57] ABSTRACT

A ruthenium-free catalyst suitable for the conversion of carbon monoxide and hydrogen to alcohols, particularly methanol, comprises a mixture of metal oxides of the metals copper and beryllium where the atomic ratio of copper to beryllium is from about 0.01 to 1 to 20.0 to 1. A further metal M such as Th or Al may also be present, the atomic ratio of the metal M to beryllium being from about 0.1 to 1 to 7.5 to 1.

The catalyst can be employed as convert carbon monoxide and hydrogen at elevated temperature and pressure, for example 100° to 500° C. and 150 to 4000 psig, to a product rich in alcohols and low in acids and hydrocarbons.

5 Claims, No Drawings

COPPER BERYLLIUM-CONTAINING CATALYSTS FOR THE PRODUCTION OF ALCOHOLS

TECHNICAL FIELD

This invention relates to a novel catalyst, more particularly to a mixed metal oxide catalyst containing copper and beryllium, to a process for its preparation and to a process using the catalyst for the production of alcohols from carbon monoxide and hydrogen.

BACKGROUND OF THE INVENTION

The production of alcohols from carbon monoxide and hydrogen has been previously described and a variety of different catalysts have been proposed.

For example, U.S. Pat. No. 2,061,470 describes the production of methanol from carbon monoxide and hydrogen using, as catalyst, the reduction product of a fused mixture of copper oxide and manganese oxide, or copper oxide and zinc oxide and an oxide of an element selected from chromium, vanadium, zirconium, aluminum, magnesium, titanium, thorium, silicon and cerium.

Further, U.S. Pat. No. 4,298,354 discloses a mixed metal oxide catalyst containing copper, thorium, an alkali metal and at least one other metal selected from Ca, Mo, Rh, Mn, Pt, Ce, Cr, Zn, Al, Ti, La, V, U, Ru, Re and Pd and its use for the production of methanol and alcohols containing from 2 to 6 carbon atoms.

European Patent Application No. 082 692 describes a mixed oxide catalyst composition containing copper and ruthenium, optionally a metal selected from Ce, Cr, Fe, Mn, Mo, Th and Zn and optionally an alkali metal or alkaline earth metal. The catalysts are described for the conversion of carbon monoxide and hydrogen to a product mixture containing carboxylic acids, hydrocarbons and alcohols. The products obtained from the use of this catalyst contain large amounts of carboxylic acids and hydrocarbons, the amounts of each of which in most cases exceed on a weight basis the amount of alcohols.

For an alcohol composition whose intended use is a motor fuel the presence of significant quantities of carboxylic acids is very undesirable. It is therefore an object of the present invention to provide a catalyst and a process in which it is used for the production of alcohols in which process significantly less acids are produced than is the case using the copper-ruthenium catalysts disclosed in the above mentioned European patent application.

SUMMARY OF THE INVENTION

According to one aspect of the present invention a ruthenium-free catalyst suitable for the conversion of carbon monoxide and hydrogen to alcohols comprises a mixed metal oxide containing the metals copper and beryllium wherein the atomic ratio of copper to beryllium is from about 0.01 to 1 to about 20.0 to 1.

The catalyst may contain a further metal M selected from the group consisting of Th, Pd, Mn, Cr, Fe, Co, Zn, Ce, V, Ni, Rh, Al, Re, Os, Pt, Ir, Ag, Ti, La, Si, U, Pr, Nd, Zr, Sc and Eu.

According to another aspect of the invention a process for the production of alcohols comprises reacting carbon monoxide and hydrogen at elevated temperature and pressure in the presence of a ruthenium-free mixed metal oxide catalyst containing the metals copper and beryllium wherein the atomic ratio of copper to beryllium is from about 0.01 to 1 to about 20.0 to 1.

The catalyst can be represented by the formula $$Cu_a Be M_b A_c O_x$$

wherein

M is selected from the group consisting of Th, Pd, Mn, Cr, Fe, Co, Zn, Ce, V, Ru, Ni, Rh, Al, Re, Os, Pt, Ir, Ag, Ti, La, Si, U, Pr, Nd, Zr, Sc, and Eu or a mixture of two or more thereof, A is an alkali or alkaline earth metal or a mixture of alkali and/or alkaline earth metals, a is from about 0.01 to about 20.0 b is from about 0.0 to about 7.5 c is from about 0.01 to about 10.0 and x is the number of oxygens needed to fulfill the valence requirements of the other elements.

In stating that the valence requirements of the other elements for oxygen are satisfied, we do not intend to exclude catalysts where one or more of the other elements is present in an elemental or zero valent state, provided there is some chemically bound oxygen in the catalyst. Further, the above formula is not intended to be limited to catalysts containing only the elements specified above for M and A in combination with copper and beryllium, but includes the optional presence of elements other than those specified.

DESCRIPTION OF THE PREFERRED EMBODIMENTS

Catalyst:

In the formula $Cu_a Be M_b A_c O_x$

M is preferably Al or Th,

A is preferably Na or K, a is preferably from 0.5 to 7.5, b is preferably from 0.2 to 5.0, c is preferably from 0.1 to 5.0.

The catalyst of the present invention is a mixed-metal oxide. In the process of the invention, this catalyst is preferably utilized in a partally reduced state. However, this catalyst is not totally reduced to elemental metal and contains chemically bound oxygen.

The catalyst may be prepared by first mixing compounds containing the metals in a liquid solution or slurry, (e.g., a water solution or slurry), and heating. The catalyst precursor is recovered from the liquid then dried and calcined. Suitable compounds containing the metals include but are not limited to oxides, hydroxides, inorganic salts (e.g., nitrates, phosphates, halides, carbonates, silicates, aluminates) and salts of organic acids (e.g., acetates formates, butyrates, prepionates, benzoates and the like).

Preferred catalysts of the invention are prepared by recovering the catalyst percursor by adding to the aqueous solution of copper and beryllium and M metal (if any) components, an alkali metal hydroxide or carbonate to cause precipitation of the catalyst precursor, heating in the presence of the alkali metal, and thereafter filtering, washing, drying and calcining the precipitate.

These catalysts may be formed in any conventional manner, such as tableting, pelleting, or supporting the active catalyst material on a carrier. The carrier is preferably inert and may include graphite, silica, alumina, Alundum, clay, alumina-silica, silicon carbide, zeolite, and the like.

A particularly useful coating procedure is disclosed in U.S. Pat. No. 4,077,912, which is incorporated herein by reference. Briefly, this method involves partially wetting the carrier, contacting the partially wetted carrier with a powdered precipitate of the catalytic components, then gently agitating the mixture until the catalyst is formed. Agitation is conveniently conducted by placing the partially wetted carrier in a rotating drum and adding the powdered precipitate until none is taken up by the carrier. The catalytic components can also be impregnated on the carrier by depositing a solution containing the catalytic components on the carrier using known techniques, then drying and calcining.

The catalytic components may optionally be individually coated or impregnated on a carrier using the above-indicated techniques.

Reactants:

The material being reacted in accordance with the present invention to form the alcohols is a gaseous mixture of hydrogen and carbon monoxide. It is preferably synthesis gas. As is well known, synthesis gas is composed basically of a mixture of hydrogen and carbon monoxide in which the $H_2/CO$ ratio is from about 1:10 to about 10:1, preferably from about 1:3 to about 3:1. It is normally derived by heating coke in the presence of air and then steam. Alternately, it can also be produced by partial combustion of coal, natural gas or petroleum hydrocarbons. It is sometimes referred to as "water gas". Synthesis gas normally contains a very low amount of sulfur compounds. It also may contain small amounts of carbons dioxide, nitrogen and other inerts.

Although synthesis gas is a preferred reactant, any other gas composed primarily of hydrogen and carbon monoxide and having an $H_2$ to CO ratio of about 1:10 to about 10:1, preferably about 1:3 to about 3:1, can be employed. The gaseous reactants should contain as little sulfur compounds as possible since sulfur is a known poison for copper containing catalysts. Preferably the gaseous reactants are essentially sulfur-free.

Reaction Mode and Conditions:

The inventive process is carried out by contacting the gaseous reactant with the inventive catalyst as described below in a suitable reactor. The reaction can be carried out in any suitable reactor configuration such as fluid bed, fixed bed or slurry reactor, continuously or in batch mode.

The contact time of the reactants with the catalyst is not critical but should be below about 200 seconds and preferably between about 5 and 100 seconds.

The reaction pressure should normally be in the range of about 150 to about 4000 psig, preferably about 700 to about 2000 psig. Although there is no real upper limit to the reaction pressure, pressures higher than about 1500 psig or 2000 psig are normally not employed because of the high expense involved. It is preferable to operate at at least about 500 psig because formation of alcohols is favored at higher pressures.

The reaction temperature should be maintained in the range of about 100° to 500° C., preferably about 220° to about 350° C., and more preferably about 250° to about 325° C.

An advantage of the process of this invention is that the temperatures and pressures employed are significantly lower than temperatures and pressures necessary in most prior art processes for producing alcohols from synthesis gas.

The space velocity of the gaseous reactant is not critical but should be about 1000 to about 100,000, preferably about 2000 to about 20,000 liters of gaseous reactant per liter of catalyst per hour.

Product:

The products produced in accordance with the process of the present invention are predominantly alcohol mixtures containing a major amount of methanol and significant amounts of higher alcohols usually having 2 to about 8, preferably 2 to about 6 carbon atoms. Normally, the alcohol products of the present invention contain about 40 percent to about 85 percent methanol, although higher amounts of methanol may be included in the product if reaction temperature is too low or if the catalyst contains additional elements fostering the generation of higher amounts of methanol than normal.

The alcohol mixtures produced by the inventive process preferably contain no more than about 85 percent by weight methanol and can be directly added to gasoline. The portion of the alcohol product other than methanol is a mixture composed primarily of 2 to about 6 carbon atom alcohols. The alcohols are composed almost completely of isoalcohols and normal alcohols with the iso to normal ratio being in the range of about 0.01 to about 20. Preferably, substantially no tertiary alcohols are present.

The product alcohol mixtures of the present invention are useful in extending gasoline. They can be mixed with gasoline in any amount, and when present in amounts of less than about 25 percent by weight of the gasoline/alcohol mixture, no significant effect on the operation of an internal combustion engine containing the gasoline/alcohol mixture is noticed. Furthermore, the mixed alcohol products of the present invention can be mixed with any type of gasoline be it substantially all paraffinic such as alkylate or highly aromatic. Moreover, if the product alcohol mixtures employed have no more than about 85 percent by weight methanol, the resultant gasoline/alcohol mixture can tolerate significant amounts of water without phase separation.

Alcohol mixtures produced in accordance with this invention containing more than about 85 percent methanol, for example up to about 95 percent methanol or more, can be used for addition to gasoline if such mixtures are blended with higher alcohols to provide a mixture with an overall methanol level of about 85 percent or less. These alcohol mixtures can be distilled to remove a sufficient amount of methanol to provide a mixture with a methanol level of about 85 percent or less.

In order to further illustrate the catalyst and process of the present invention, the following examples are provided:

EXAMPLE 1

Preparation of Copper-Beryllium Catalyst

To 1.25 liters of distilled water were added 66.93 grams to copper nitrate ($Cu(NO_3)_2 \cdot 2.5\ H_2O$, f.w. 232.1, 0.2877 mole Cu), and 35.88 grams of beryllium nitrate ($Be(NO_3)_2 \cdot 3\ H_2O$, f.w. 187.1, 0.1918 mole Be) and the mixture was heated to 90° C. while stirring vigorously. The pH was raised to 9.5 by the addition of hot 2M $K_2CO_3$ in distilled water and the pH was monitored by testing with wide-range pH paper. The endpoint was determined by testing with narrow-range pH paper. The mixture was digested at 90° C. for an hour and then allowed to cool to room temperature. The room temperature mixture was neutralized to pH 7.0 by addition of 2M $HNO_3$ while stirring. The solid was allowed to settle overnight and the supernatant was removed by decantation. The solid was re-slurried with 1 liter of distilled water and stirred then allowed to settle again. The washing procedure was repeated four times and then the resulting solid was separated by vacuum filtration and sucked dry. It was dried further by heating at 110° C. overnight and calcining in air at 400° C. for 4 hours. The finished catalyst was crushed to fine material and pelletized by adding 5 weight percent of graphite and pressing in a pellet press. The pellets were ground to give 10–30 mesh material.

The catalyst thus prepared had the following weight chemical analysis:
Cu 62 percent
Be 4.9 percent
K 0.9 percent
corresponding to a formula $Cu_{1.5}BeK_{0.4}O_x$.

EXAMPLE 2

Preparation of Copper-Beryllium-Thorium Catalyst 47.40 g of $Cu(NO_3)_2 \cdot 2.5\ H_2O$ (0.2038 mole Cu), 75.00 g of $Th(NO_3)_4 \cdot 4\ H_2O$ (0.1358 mole Th), and 7.62 g of $Be(NO_3)_2 \cdot 3\ H_2O$ (0.0408 mole Be) were dissolved in 1¼ liters of distilled water. The mixture was heated to about 90° C. on a hotplate and was vigorously stirred with a mechanical stirrer. The pH was monitored by a narrow range pH paper. Next, hot 2M $K_2CO_3$ solution was added dropwise until the pH was approximately 9.5, then the mixture was maintained at about 90° C. for an additional one hour, then was cooled to room temperature. After cooling, the pH of the mixture was adjusted to about 7.0 with 2M $HNO_3$ then the solid was allowed to settle overnight. The clear supernatant solution above the solid was decanted and the precipitate reslurried with one liter of hot distilled water and again allowed to resettle. This washing procedure was conducted a total of 4 times, then the solid was vacuum filtered, dried overnight at 110° C., then calcined for 4 hours at 400° C. The finished catalyst was pelletized with about 5 percent graphite.

Analysis of the catalyst corresponded to a formula:

$Cu_{5.0}\ Be\ Th_{3.3}\ K_2\ O_y$

EXAMPLE 3

Preparation of Copper-Beryllium Aluminum Catalyst 200.79 g of $Cu(NO_3)_2 \cdot 2.5\ H_2O$ (0.8631 mole Cu), 107.64 g of $Be(NO_3)_2 \cdot 3\ H_2O$ (0.5754 mole Be), and 43.17 g of $Al(NO_3)_3 \cdot 9\ H_2O$ (0.1151 mole Al) were dissolved in 2.5 liters of distilled water and heated to about 90° C. Next, while vigorously stirring the nitrate solution, a hot (about 60° C.) 2M $K_2CO_3$ solution was added dropwise until the pH of the mixture registered about 9.5 on a narrow range (6.0–9.5) pH paper. The pH of the mixture was maintained at about 9.5 and at about 90° C. for an additional one hour, then it was cooled to room temperature. The pH was adjusted to 7.0 with dilute $HNO_3$ then allowed to settle overnight. The supernatant liquid was decanted off the top with an aspirator arrangement and an additional one liter of distilled water added. The mixture was then vigorously stirred and heated up to about 60° C. The slurry was vacuum filtered until the filter cake was almost dry. Next, the filter cake was washed twice more by first reslurrying with one liter portions of distilled water then vacuum filtering. The filter cake was then dried for about 3 hours at 110° C., then calcined at 400° C. for 4 hours. The catalyst was pelletized with about 5 percent by weight of graphite.

Analysis of the catalyst corresponded to the formula:

$Cu_{1.5}\ Be\ Al_{0.2}\ K_x\ O_y$

EXAMPLES 4 TO 16

Prior to commencing the alcohol synthesis processes, each catalyst was ground to a 10–30 mesh size, loaded in a reactor of 20 cc capacity and reduced under an atmosphere of 15 percent $H_2$ and 85 percent $N_2$ by initially heating over a 1–2 hour period to 250° C. and maintaining a temperature of 250° C. for one hour. The reactor was then cooled to room temperature and pressurized to 750 psig with a 1:1 molar mixture of $H_2/CO$. The flow was adjusted to provide a space velocity of 3000 liters of gaseous reactant per liter of catalyst per hour. The reactor was then heated over a 1.5-hour period to the operating temperature. After about 1 to 1.5 hours of reaction, the off-gas (effluent) was sampled and analyzed and the condensible product diverted from a pre-run receiver to a product collection receiver. A recovery run proceeded for one to three hours during which time the off-gas was analyzed by gas chromatography and its volume measured. The liquid product was weighted and analyzed. In some instances, the catalyst was tested at more than one operating temperature. When this was done, the temperature of the reactor was changed over a 30-minute period and an equilibration period of 30–90 minutes was then allowed. The above-indicated procedures for the recovery run were then repeated. The results obtained are tabulated in the following Tables 1 and 2.

TABLE 1

|  | EXAMPLE NO. | | | | | |
|---|---|---|---|---|---|---|
|  | 4 | 5 | 6 | 7 | 8 | 9 |
| Catalyst from Example No. | 1 | 1 | 1 | 1 | 1 | 1 |
| Temperature °C. | 285 | 300 | 325 | 225 | 250 | 270 |
| SV/ V/V/hour | 2667 | 2667 | 2667 | 10,000 | 10,000 | 10,000 |
| Pressure Psig | 1000 | 1000 | 1000 | 750 | 750 | 750 |
| Run Time Hours | 2 | 2 | 2 | 0.75 | 0.75 | 0.75 |
| H$_2$/CO Molar ratio | 1 | 1 | 1 | 2 | 2 | 2 |
| Liq wt g | 12.2 | 9.1 | 3.4 | 5.1 | 9.6 | 8.7 |
| % C1OH | 82.7 | 83.0 | 82.5 | 93.3 | 90.2 | 87.5 |
| % C2OH | 4.0 | 4.1 | 3.5 | 1.7 | 2.8 | 3.2 |
| % n C3OH | 3.7 | 4.1 | 3.5 | 0.4 | 1.5 | 2.0 |
| % i C3OH | 0.4 | 0.4 | 0.4 | 0.3 | 0.4 | 0.4 |
| % n C4OH | 0.3 | 0.3 | 0.9 | 0.0 | 0.2 | 0.4 |
| % i C4OH | 1.4 | 2.0 | 2.3 | 0.0 | 0.3 | 0.4 |
| % n C5OH | 0.5 | 0.6 | 0.6 | 0.0 | 0.2 | 0.2 |
| % i C5OH | 0.6 | 0.7 | 0.8 | 0.0 | 0.0 | 0.2 |
| % n C6OH | 0.0 | 0.0 | 0.3 | 0.0 | 0.0 | 0.2 |
| % i C6OH | 0.3 | 0.4 | 0.3 | 0.0 | 0.0 | 0.0 |
| Wt CH$_4$ g | 1.0 | 1.1 | 1.4 | 0.04 | 0.15 | 0.3 |
| Wt CO$_2$ g | 6.9 | 7.5 | 9.4 | 0.7 | 1.8 | 2.2 |
| Prod g/l/hour | 339 | 253 | 93 | 381 | 707 | 645 |
| HA/HC | 1.4 | 1.1 | 0.3 | 8.0 | 6.4 | 2.5 |

TABLE 2

|  | EXAMPLE NO. | | | | | |
|---|---|---|---|---|---|---|
|  | 10 | 12 | 13 | 14 | 15 | 16 |
| Catalyst from Example No. | 2 | 2 | 2 | 3 | 3 | 3 |
| Temperature °C. | 285 | 300 | 325 | 285 | 300 | 325 |
| SV/ V/V/hour | 2400 | 2400 | 2400 | 2400 | 2400 | 2400 |
| Pressure Psig | 1000 | 1000 | 1000 | 1000 | 1000 | 1000 |
| Run Time Hours | 2 | 2 | 2 | 2 | 2 | 2 |
| H$_2$CO Molar ratio | 1 | 1 | 1 | 1 | 1 | 1 |

TABLE 2-continued

| | EXAMPLE NO. | | | | | |
|---|---|---|---|---|---|---|
| | 10 | 12 | 13 | 14 | 15 | 16 |
| Liq wt g | 12.1 | 9.9 | 6.0 | 11.6 | 8.6 | 4.5 |
| % C1OH | 77.3 | 70.2 | 59.8 | 83.6 | 76.1 | 78.9 |
| % C2OH | 4.5 | 4.8 | 3.8 | 3.5 | 3.7 | 3.6 |
| % n C3OH | 4.9 | 6.4 | 7.4 | 3.3 | 4.0 | 4.1 |
| % i C3OH | 0.4 | 0.4 | 0.3 | 0.3 | 0.3 | 0.3 |
| % n C4OH | 1.0 | 1.2 | 1.4 | 0.7 | 0.8 | 1.0 |
| % i C4OH | 2.0 | 3.9 | 11.0 | 1.6 | 2.5 | 4.1 |
| % n C5OH | 0.6 | 0.9 | 1.6 | 0.7 | 0.5 | 0.7 |
| % i C5OH | 1.0 | 1.5 | 2.9 | 0.0 | 0.8 | 1.2 |
| % n C6OH | 0.4 | 0.5 | 0.5 | 0.4 | 0.0 | 0.0 |
| % i C6OH | 0.7 | 1.0 | 1.7 | 0.0 | 0.4 | 0.4 |
| Wt CH$_4$ g | 0.7 | 0.8 | 1.0 | 0.5 | 0.7 | 0.8 |
| Wt CO$_2$ g | 6.5 | 8.1 | 10.8 | 4.8 | 5.6 | 7.3 |
| Prod g/l/hour | 303 | 247 | 149 | 289 | 215 | 112 |
| HA/HC | 2.8 | 2.6 | 1.8 | 2.3 | 1.7 | 0.84 |

In the above tables, the abbreviations are as follows:

SV means space velocity in volumes of gas per volume of catalyst per hour.

Liq Wt means weight of liquid product in grams.

C1OH means an alcohol containing one carbon atom i.e. methanol.

C2OH means an alcohol containing two carbon atoms.

C3OH, C4OH, C5OH and C6OH have corresponding meanings.

n and i mean normal and iso respectively.

wt CH$_4$ means weight of methane gas produced in grams.

wt CO$_2$ means weight of carbon dioxide gas produced in grams.

Prod g/l/hour means productivity measured in grams of liquid product per liter of catalyst per hour.

HA/HC means the weight ratio of higher alcohols i.e. alcohols containing 2 or more carbon atoms to hydrocarbons.

The above results demonstrate that (a) the catalysts are active for the preparation of alcohols, particularly methanol, from syn gas, and (b) at least 85% by weight of the liquid product is in the form of alcohols with less than 15% being composed of esters, acids, aldehydes and water. A higher percentage of the liquid product is therefore provided by alcohols than is the case with the ruthenium containing catalysts of European Patent Application No. 082692.

Moreover, substantially no hydrocarbons other than methanol were detected in the tail gas from the reactor. This demonstrates that the amount of hydrocarbons produced is significantly less than is produced using the copper ruthenium containing catalysts of European Patent Application No. 082692. The catalysts of the present invention therefore have two important technical advantages over those disclosed in the above mentioned European patent application.

We claim:

1. A ruthenium-free catalyst represented by the formula $$Cu_a\ Be\ M_b\ A_c\ O_x$$

where

M is selected from the group consisting of Th, Pd, Mn, Cr, Co, Zn, Ce, V, Ni, Rh, Al, Re, Os, Pt, Ir, Ag, Ti, La, Si, U, Pr, Nd, Zr, Sc and Eu, A is an alkali metal or alkaline earth metal other than Be and a is from about 0.01 to about 20.0 b is from 0.0 to about 7.5 c is from 0.01 to about 10.0 and x is a number such that the valence requirements of the other elements for oxygen is satisfied.

2. The ruthenium-free catalyst as claimed in claim 1 wherein M is selected from Th and Al.

3. The ruthenium-free catalyst as claimed in claim 1 wherein a is from about 0.5 to about 7.5.

4. The ruthenium-free catalyst as claimed in claim 1 wherein b is from about 0.2 to about 5.0.

5. The catalyst as claimed in claim 1 wherein A is an alkali metal.

* * * * *